US008605276B2

(12) United States Patent
Wu et al.

(10) Patent No.: US 8,605,276 B2
(45) Date of Patent: Dec. 10, 2013

(54) ENHANCED DEFECT SCANNING

(75) Inventors: Chih-Jen Wu, Chu-Dong Town (TW);
Chen-Ming Huang, Hsinchu (TW);
Kuan-Chieh Huang, Hsinchu (TW);
Chi-Yuan Shih, Hsinchu (TW);
Chin-Hsiang Lin, Hsin-Chu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 100 days.

(21) Appl. No.: 13/286,617

(22) Filed: Nov. 1, 2011

(65) Prior Publication Data

US 2013/0107248 A1      May 2, 2013

(51) Int. Cl.
*G01N 21/00* (2006.01)
*G01N 21/95* (2006.01)

(52) U.S. Cl.
CPC ................................. *G01N 21/9501* (2013.01)
USPC .................... 356/237.4; 356/237.2; 356/237.3

(58) Field of Classification Search
CPC ........................... G01N 21/00; G01N 21/9501
USPC ............................................ 356/237.1–237.5
See application file for complete search history.

(56) References Cited

U.S. PATENT DOCUMENTS

| 6,097,484 | A   | * | 8/2000 | McIntosh et al. | ........... 356/237.5 |
| 7,298,496 | B2  | * | 11/2007 | Hill | ............................... 356/512 |
| 7,372,561 | B2  | * | 5/2008 | Shibata et al. | ............. 356/237.5 |
| 2010/0201983 | A1 | * | 8/2010 | Hatano et al. | ................. 356/337 |

* cited by examiner

*Primary Examiner* — Michael P Stafira
(74) *Attorney, Agent, or Firm* — Haynes and Boone, LLP (57) ABSTRACT

One of the broader forms of the present disclosure involves a method of enhanced defect inspection. The method includes providing a substrate having defect particles and providing a fluid over the substrate and the defect particles, the fluid having a refractive index greater than air. The method further includes exposing the substrate and the defect particles to incident radiation through the fluid, and detecting, through the fluid, radiation reflected or scattered by the defect particles.

18 Claims, 11 Drawing Sheets

ENHANCED DEFECT SCANNING

TECHNICAL FIELD

The present disclosure relates generally to inspection of a substrate, and more particularly, to enhanced contamination or defect inspection of a substrate.

BACKGROUND

Substrate processing, e.g., semiconductor wafer fabrication, often requires that substrates be substantially free of defects. Defect detection systems are often employed as part of the manufacturing process to locate defects on a substrate. Certain types of defect detection systems may be calibrated using a deposition of standard defect particles, such as polystyrene latex (PSL) spheres, silicon oxide particles, or other calibration spheres, as a known source of scatter signal. Radiation is directed toward a calibration sample substrate having calibration spheres of a known size distribution deposited on its surface. The measured amplitude of radiation scattered by the calibration spheres may be used as a standard for matching the response of a defect detection system to a known source of scattering. The use of a deposition of calibration spheres as a known source of scatter signal allows meaningful comparisons to be made between scatter signals from calibration spheres as measured by bright or dark field detection scanning surface inspection systems of different designs. The measured calibration scatter signal amplitude may be compared to scatter signals for a sample substrate having real surface defects whose identity and true size are unknown. This practice provides a basis for quantifying system performance as used in related standards concerned with parameters such as sensitivity, repeatability and capture rate.

As the size of semiconductor integrated circuit features decreases, detection of increasingly smaller defects becomes more critical. As a result, shorter wavelength radiation may be used to detect smaller defects. However, a scanning inspection system may have a limited light source or a weak signal may result from the use of shorter wavelength radiation.

SUMMARY

The present disclosure provides for various advantageous inspection systems and methods of calibrating or operating such inspection systems. One of the broader forms of the present disclosure involves a method of enhanced defect inspection. The method includes providing a substrate having defect particles and providing a fluid over the substrate and the defect particles, the fluid having a refractive index greater than air. The method further includes exposing the substrate and the defect particles to incident radiation through the fluid, and detecting, through the fluid, radiation reflected or scattered by the defect particles.

Another of the broader forms of the present disclosure involves a method of inspecting a standard mask, the method comprising: providing a substrate having standard defect particles; providing a fluid over the substrate and the standard defect particles, the fluid having a refractive index greater than air; exposing the substrate and the standard defect particles to incident radiation through the fluid; and detecting, through the fluid, radiation reflected or scattered by the standard defect particles.

Yet another of the broader forms of the present disclosure involves a system for defect inspection. The system includes a stage holding a substrate having defect particles and a fluid disposed over the substrate and the defect particles, a light source exposing the substrate and the defect particles to incident radiation through the fluid, and a detector detecting, through the fluid, radiation reflected or scattered by the defect particles.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Various features may be arbitrarily drawn in different scales for the sake of simplicity and clarity. It is noted that the same or similar features may be similarly numbered herein for the sake of simplicity and clarity.

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Embodiments of the present disclosure utilize a fluid over contamination defects or simulated contamination defects for decreased incident radiation wavelengths and increased reflected or scattered radiation signals, thereby enhancing defect inspection analysis. In one example, the fluid has a refractive index greater than the refractive index of air.

Simulated or standard defect particles should be stable over time under exposure to ultraviolet or other radiation for calibration of a substrate inspection tool. Calibration of a defect detection system is largely a matter of exposing the simulated defects on the surface of the substrate to radiation having a wavelength that is sufficiently short to be significantly scattered by the simulated defects. The amplitude of the radiation scattered by the simulated defects is measured and associated with a nominal size of the simulated defects. Calibration using the simulated defects may be performed, e.g., as described in ASTM standard: F1620-96, "Standard Practice for Calibrating a Scanning Surface Inspection System Using Monodisperse Polystyrene Latex Spheres Deposited on Polished or Epitaxial Wafer Surfaces", (Withdrawn 2003), ASTM International, 2003, which is incorporated herein by reference.

After calibration, the system may then be used to measure scattering signals from localized light scatter on a test substrate. Previously, the scattering signal may have been expressed in terms of a latex sphere equivalent (LSE), which refers to the diameter of a monodisperse polystyrene latex sphere that produces the same detected scattering intensity as the localized light scatter (LLS) under investigation under identical test conditions. In accordance with the present disclosure, a scattering signal may be expressed in terms of a simulated contamination defect equivalent (SCDE), which refers to the diameter of a simulated contamination defect sphere or standard defect particle that produces substantially the same detected scattering intensity as the LLS under investigation under substantially identical test conditions.

Figure 1:
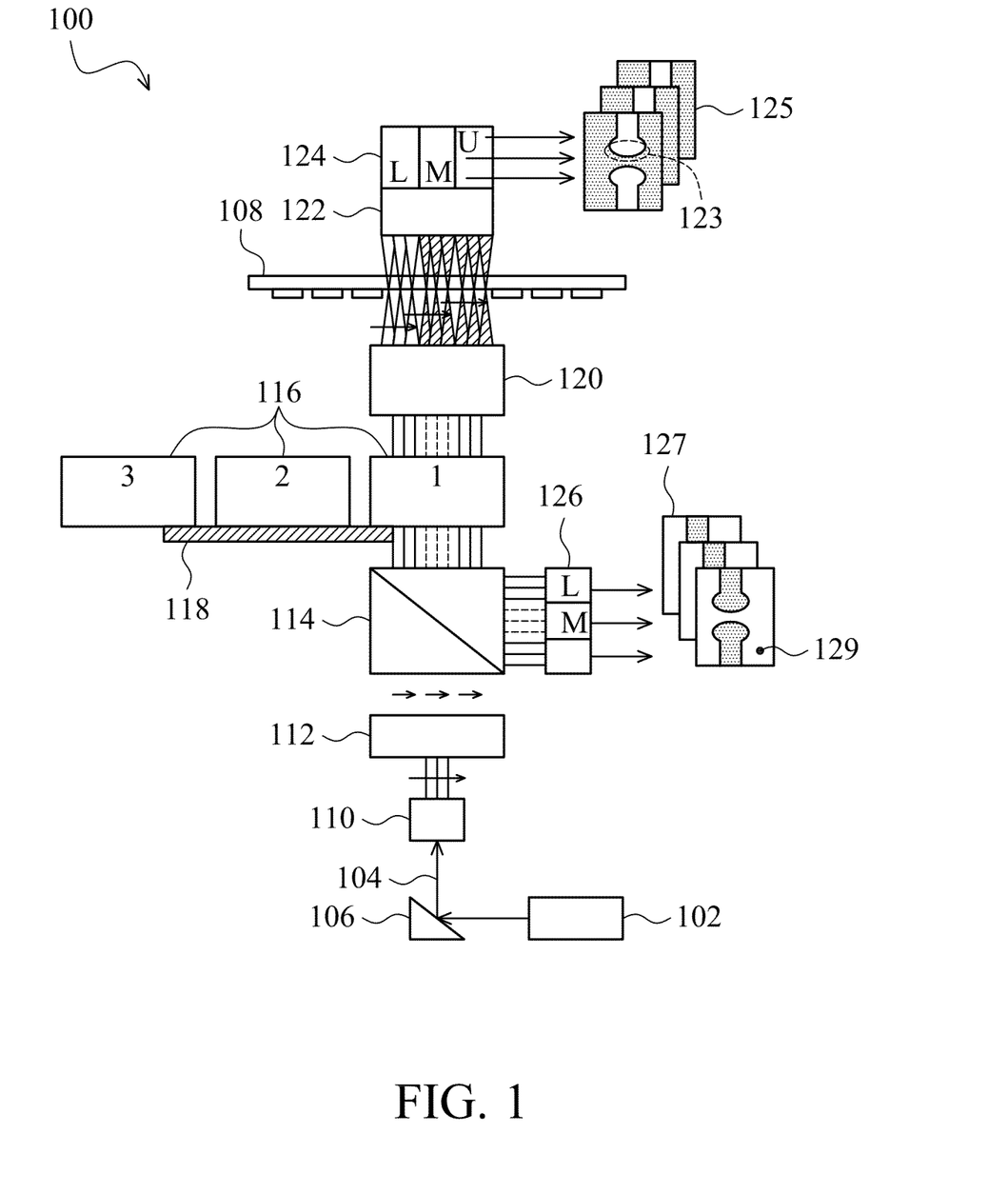
FIG. 1 is a cross-sectional schematic diagram of a sample inspection system that may be used in embodiments of the present disclosure.

By way of example, FIG. 1 is a schematic view of a scanning surface inspection system (SSIS) 100 illustrating an example of a general set up for a sample inspection system that may be used with embodiments of the present disclosure. By way of example, the system 100 may be a bright field imaging system. In addition, embodiments of the present disclosure may be used in conjunction with other bright field imaging system designs. An example of such an alternative implementation is described below with respect to FIG. 4. In addition, certain embodiments of the present invention may also be used with so-called "dark field" inspection systems. In addition, various wafer scanning systems may be used such as a scanning electron microscope (SEM) system, an optical microscope system, a scanning probe microscope system, laser microscope system, transmission electron microscope system, focus ion beam microscope system, or other suitable optical imaging systems.

In the system 100, a radiation source 102 may provide incident radiation 104 at one or more wavelengths in a wide electromagnetic spectrum (including but not limited to deep ultraviolet (DUV), ultraviolet (UV), visible, infrared and the like). In one embodiment, the radiation source 102 provides the incident radiation 104 as an electron-beam (e-beam). In another embodiment, the radiation source 102 may be a laser providing the incident radiation 104 in the form of a laser beam. A beam steering mechanism 106 and other optical components may steer the incident radiation 104 such that the incident radiation 104 is normally incident on a substrate 108 such as a wafer, mask, or reticle. The substrate 108 may be mounted to a stage that allows for indexing and scanning of the substrate. In some embodiments of the present invention, the substrate 108 may be a pattern defect substrate. In other embodiments, simulated contamination defects UV-resistant silicon dioxide may be disposed on a surface of the substrate 108, as further described below.

Additional optical components may be disposed between the beam steering mechanism 106 and the substrate 108. For example an acoustic scanner 110 may separate the incident radiation into multiple beams. A beam replicator 112 may replicate each of these beams in different wavelength ranges. The replicated beams may optionally pass through an optical circulator 114 and one or more pixel filters 116. The pixel filter 116 is an optical subsystem that creates various pixel sizes. Smaller pixels are used to achieve sensitivity for smaller defects. In some systems, multiple filters 116 may be mounted to a turret 118 for quick replacement. Alternatively, different pixel sizes may be obtained through use of a zoom lens system. After passing through the pixel filters 116, the replicated beams are focused by an imaging objective 120 onto a surface of the substrate 108. Other suitable optical components may be additionally or alternatively disposed between the beam steering mechanism 106 and the substrate 108.

Collection optics 122 mounted opposite the objective 120 may collect radiation transmitted by the substrate 108 and couple the transmitted radiation to photosensors 124. Signals from the photosensors 124 can be used to generate images 125 of the substrate 108 from the detected transmitted radiation. Radiation reflected by the substrate may be collimated by the imaging objective 120 and deflected by the optical circulator 114 to another set of photosensors 126. Signals from the photosensors 126 can be used to generate images 127 of the substrate 108 from the detected transmitted radiation. In a pattern defect mode, the system 100 may detect malformations in a mask pattern on the substrate 108 from the images 125 obtained using transmitted light or the images 127 obtained using reflected light. The pattern defect mode is used with a pattern defect substrate or standard mask having a simulated mask pattern with simulated defects at known locations. The pattern defect mode is used to detect defects 123 in a mask pattern, e.g., missing parts of the pattern or relatively large defects in the pattern that are attached to or close to other parts of the pattern. In a contamination mode of the system 100, contaminants on the surface of the substrate 108 (e.g., a test substrate) may be detected by comparing the images 125 and 127. For example, a feature 129 appearing in image 127 but not in image 125 may be marked as a contaminant.

By way of example, a calibration standard (e.g., a standard mask) may use simulated defects in the form of UV-resistant silicon oxide particles. Such UV-resistant silicon oxide particles may be used to calibrate both bright field and dark field inspection tools. There are a number of different ways of producing simulated defects that are resistant to radiation having a wavelength of about 260 nanometers or less.

As will be explained in greater detail below with respect to FIGS. 5 and 6A-6B, the substrate 108 as a test substrate or a calibration standard (e.g., a standard mask) includes a fluid layer over the substrate and the contamination defects or simulated contamination defects in one embodiment, thereby decreasing incident radiation wavelengths and increasing reflected or scattered radiation signals to enhance defect inspection analysis. In one example, the fluid has a refractive index greater than the refractive index of air.

Figure 2A:
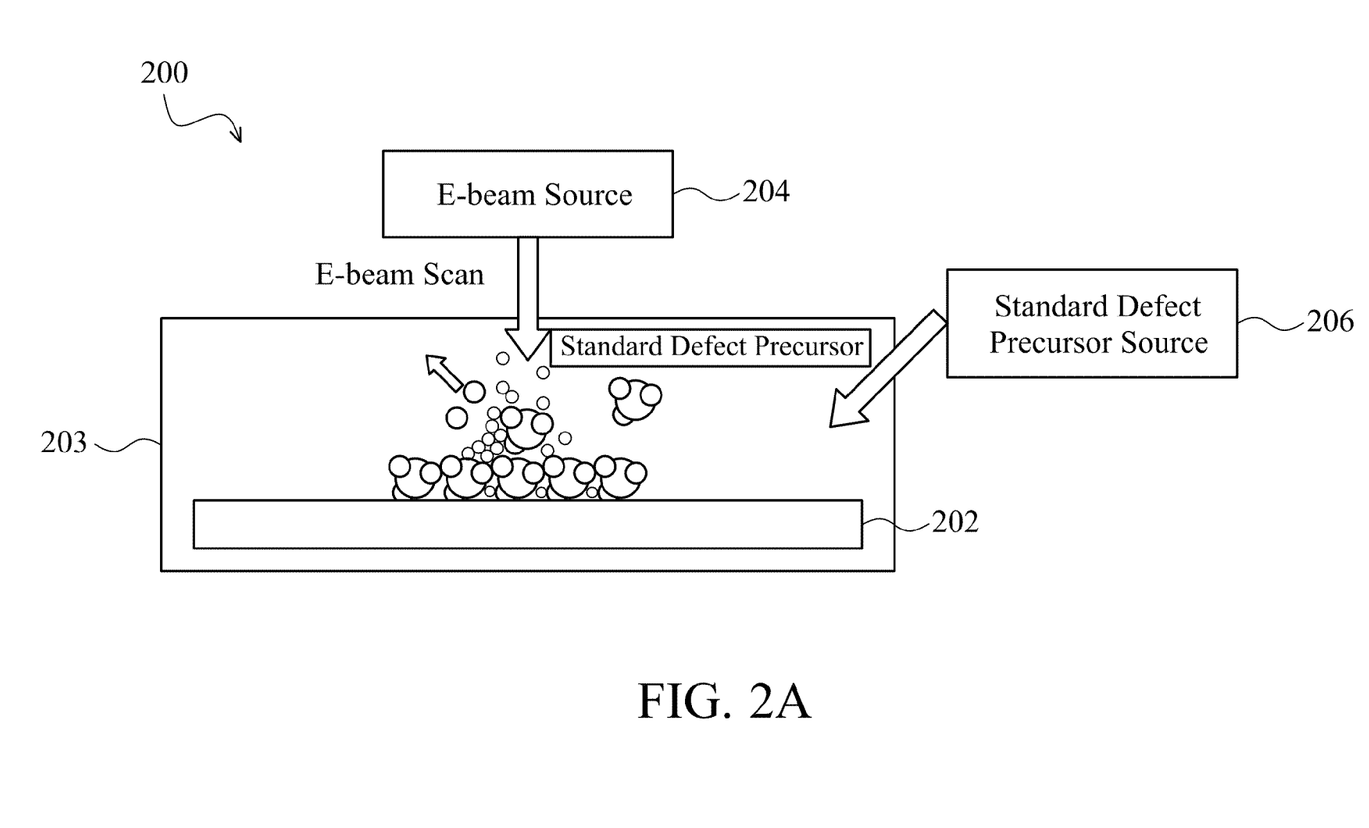
FIGS. 2A and 2B are cross-sectional schematic diagrams illustrating the formation of a standard mask coated with standard defect particles from reaction of a standard defect precursor with an electron beam.
Figure 2B:
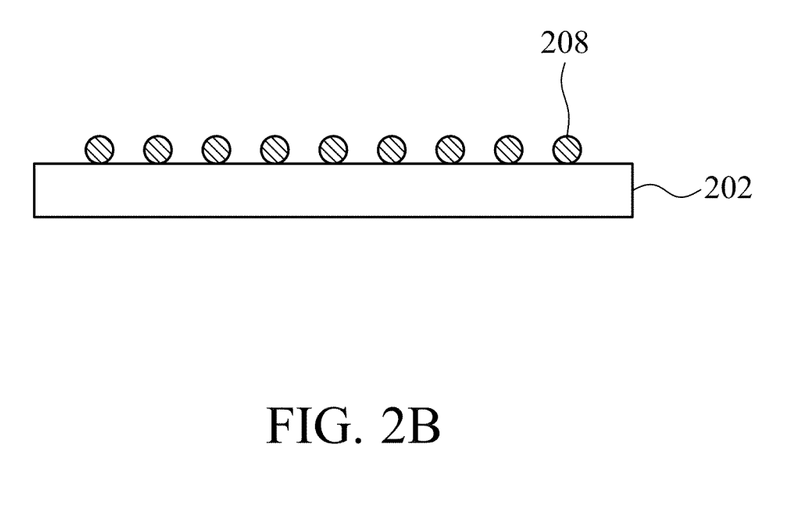
Figure 2C:
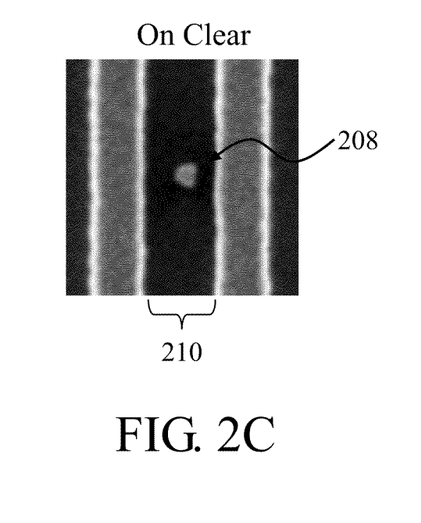
FIGS. 2C-2E are images of standard defect particles (e.g., PSL or silicon oxide particles) formed as simulated contamination defects of controlled size on a clear, a dark, and an edge location, respectively, of a standard mask pattern region.
Figure 2D:
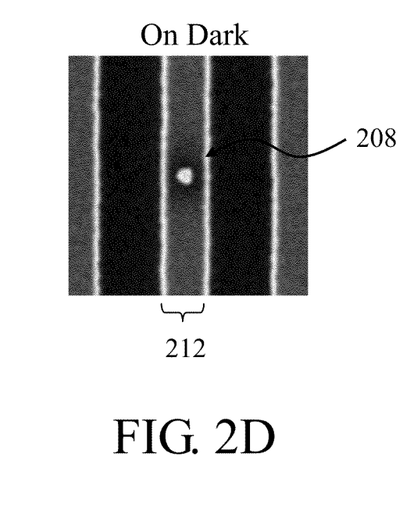
Figure 2E:
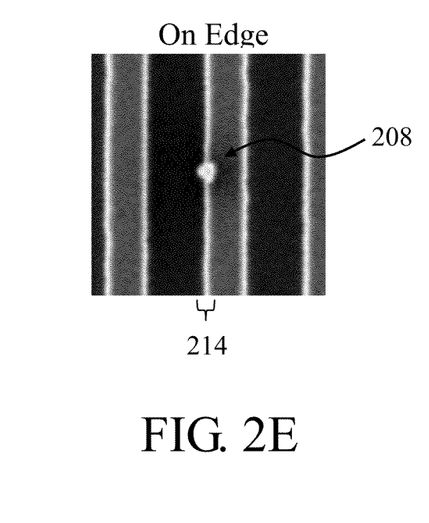

Referring now to FIGS. 2A-2E, FIGS. 2A and 2B are cross-sectional schematic diagrams illustrating a system 200 for forming a standard mask substrate 202 coated with standard defect particles 208 (e.g., silicon dioxide particles) from reaction of a precursor, such as a TEOS precursor, with an electron beam, and FIGS. 2C-2E are images of standard defect particles 208 formed as simulated contamination defects of controlled size on a clear, a dark, and an edge location, respectively, of a standard mask pattern region in accordance with aspects of the present disclosure. In other embodiments, a Cr(CO)6 precursor may be used instead of a TEOS precursor to react with an electron beam to form simulated contamination particles with similar process conditions as described above and below.

Figure 4:
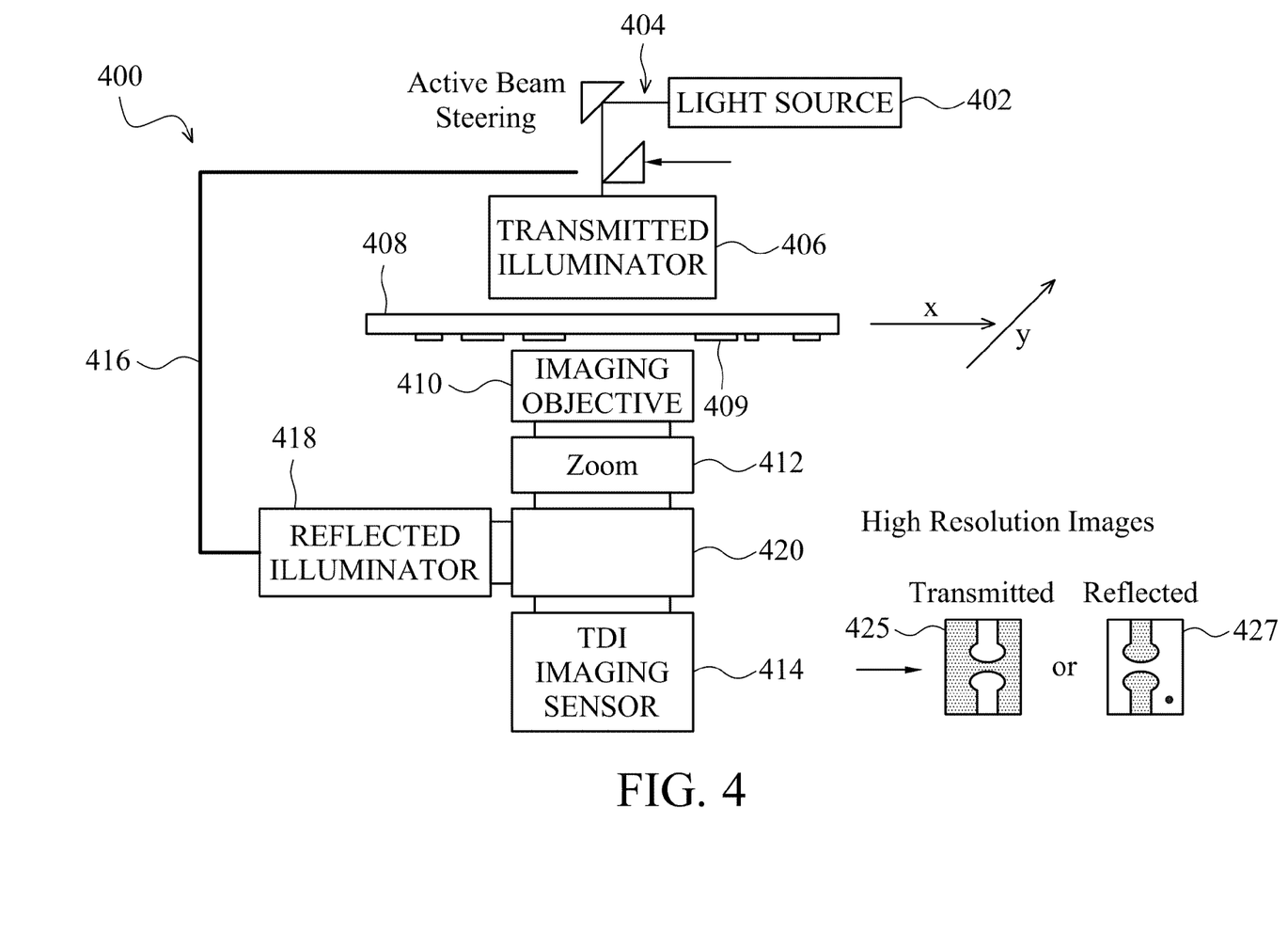
FIG. 4 is a schematic diagram illustrating a sample inspection system configured for contamination mode calibration using a pattern defect mask according to an embodiment of the present disclosure.

As shown in FIGS. 2A and 2B, standard defect particles of controlled size are formed at one or more controlled locations on substrate 202 to be used as a standard mask for an inspection system, such as system 100 of FIG. 1 or system 400 of FIG. 4. In accordance with an embodiment of the present disclosure, the substrate 202 may include a mask and/or a wafer.

In one embodiment, as shown in FIG. 2A, substrate 202 is provided within a chamber 203, and a standard defect precursor (e.g., tetraethylorthosilicate (TEOS) precursor) from a standard defect precursor source 206 (e.g., TEOS source) is provided within the chamber 203. An electron beam (e-beam) from an e-beam source 204 reacts with the precursor to form standard defect particles 208 (FIG. 2B) of controlled size at one or more controlled locations on the substrate 202, the standard defect particles 208 disposed as simulated contamination defects. E-beam source 204 and precursor source 206 are operably coupled to chamber 203 to provide a suitable e-beam and precursor, respectively, within chamber 203. In one embodiment, e-beam source 204 may be operably coupled to chamber 203 via optics to provide a scanning e-beam, and/or the substrate 202 may be provided within chamber 203 on a movable stage or platform. All or part of e-beam source 204 and precursor source 206 may be provided within or outside chamber 203. In one example, e-beam source 204 may include a Schottky field emitter or a cathode emitter, and in another example includes a Gemini® Scanning Electron Microscope available from Carl Zeiss NTS, LLC.

Thus, system 200 includes chamber 203 configured to house substrate 202, precursor source 206 coupled to the chamber 203 for providing a standard defect precursor within the chamber, and an electron beam source 204 coupled to the chamber 203, wherein the electron beam source 204 is configured to provide an electron beam within the chamber 203 for reacting the electron beam with the precursor to form standard defect particles of controlled size at one or more controlled locations on the substrate 202, the standard defect particles disposed as simulated contamination defects.

In one example, reaction of the e-beam and the TEOS precursor may follow equation (1) below to form silicon oxide particles:

$$Si(OC_2H_5)_4 \rightarrow SiO_2 + 2O(C_2H_5)_2 \quad (1)$$

In one example, the silicon oxide particle size can be well controlled by the e-beam dwell time, and the silicon oxide particle location on the substrate can be well controlled by control of the e-beam location relative to the substrate.

As shown in FIG. 2B, substrate 202 is coated with standard defect particles 208. In one embodiment, the standard defect particles 208 may be characterized by a size distribution range between 30 nm and 100 nm by controlling the electron beam scan conditions. In one example, the e-beam deposition process is controlled by beam dwell time ranges from between about 800 μs and about 3000 μs to generate oxide particles ranging in size between about 30 nm to about 100 nm under 1.0 key of accelerated voltage.

In one embodiment, the system used to deposit the silicon oxide particles may select particles in a certain narrow size range from a particle dispersion having a broader range of particle sizes. By way of example, the deposition system may include a differential mobility analyzer (DMA) to perform the size selection. An example of the use of a differential mobility analyzer for this purpose is set forth by George W. Mulholland et al. in "Modeling, Measurement, and Standards for Wafer Inspection", published in the proceedings of the Government Microcircuits Applications and Critical Technologies (GOMACTech) Conference: "Countering Asymmetric Threats," held Mar. 31 to Apr. 3, 2003 in Tampa, Fla.

In one example, a DMA may include an inner cylindrical tube having an outside radius connected to a variable high voltage DC power supply and an outer annular tube having an inside radius connected to ground. Clean sheath air flows through an axial region between the inner tube and the inner surface of the outer tube, while the charged aerosol enters this region through an axisymmetric opening in the outer tube. The positively charged particles move radially towards the center rod under the influence of an electric field. Near the bottom of the classifying region, a fraction of the air flow containing a near-monodisperse aerosol of the particles exits through a slit in the center tube. The size of particles in the monodisperse aerosol exiting the inner tube may be selected by appropriately adjusting a voltage applied between the inner and outer tubes and the sheath air flow rate.

Advantageously, the standard defect particles 208 are stable over time under exposure to radiation having a wavelength of about 260 nanometers or less.

The standard mask substrate 202 coated with standard defect particles 208 may be exposed to radiation of a known wavelength of about 260 nanometers or less during calibration of an inspection tool. An amplitude of scattering of the radiation by the standard defect particles is measured with the inspection tool. The measured scattering of the radiation of the standard defect particles may be associated with a nominal size of the standard defect particles 208.

Standard defect particles may thus be deposited on the substrate as simulated contamination defects by focused e-beam at critical features like high MEEF patterns on a standard mask so that a standard mask with programmed contamination is made. The mask can be used for monitoring inspection tool performance, confirming recipe tuning, evaluating new inspection tools and new defect disposition function, and/or checking contamination printability, to name several examples.

According to another embodiment of the present invention, the standard substrate may be a pattern defect substrate that may be used for a contamination-mode calibration of the inspection tool 100. FIGS. 2C-2D are images of silicon oxide particles formed as simulated contamination defects of controlled size on a clear region 210, a dark region 212, and an edge region 214, respectively, of a standard mask pattern in accordance with aspects of the present disclosure. Thus, the silicon oxide particles may be formed at one or more controlled locations of a clear, a dark, an edge, and/or a high mask error enhancement factor (MEEF) mask pattern region of a substrate.

Figure 3A:
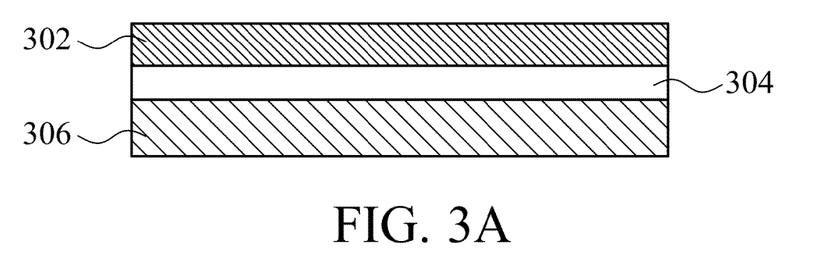
FIGS. 3A-3D are cross-sectional schematic diagrams illustrating the steps of making a pattern defect mask that may be used for contamination-mode calibration of an inspection tool according to embodiments of the present disclosure.

According to another embodiment of the present invention, FIGS. 3A-3D are cross-sectional schematic diagrams illustrating a pattern defect substrate at various stages of manufacture. FIG. 3A illustrates a starter material for making of a pattern defect substrate, which includes a phase shift layer 304 disposed between an opaque layer 302 and an optically transmissive substrate 306. In one example, the opaque layer 302 may be made of chrome. In one example, the phase shift layer 304 may be made of molybdenum silicide (MoSi) or chromium fluoride (CrF). The phase shift layer 304 may be made of or may contain a material having optical properties that are similar to those of common contaminants. Examples of optical properties that drive defect detection include, but are not limited to index of refraction and dielectric constant. Examples of classes of materials with optical properties similar to common contaminants include, but are not limited, to sulfates, e.g., ammonium sulfates, oxalates and possibly carbamates.

The optically transmissive substrate 306 may be made of quartz in one example. The optically transmissive substrate 306 can be a photomask blank. Simulated defects may be patterned into the opaque layer 302 and/or the phase shift layer 304 using a pattern generator, e.g., an e-beam or a laser. These defects may be defined in a database used to create the mask, and therefore their number, location and size may be well controlled. In addition such simulated defects may be easily sized, e.g., using Critical Dimension-Scanning Electron Microscopy (CD-SEM).

Figure 3B:
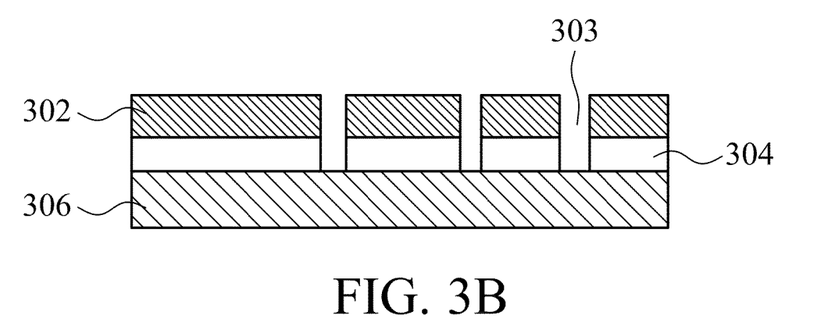

FIG. 3B illustrates a step of making holes 303 through the opaque layer 302 and the phase shift layer 304, exposing some portions of the substrate 306.

Figure 3C:
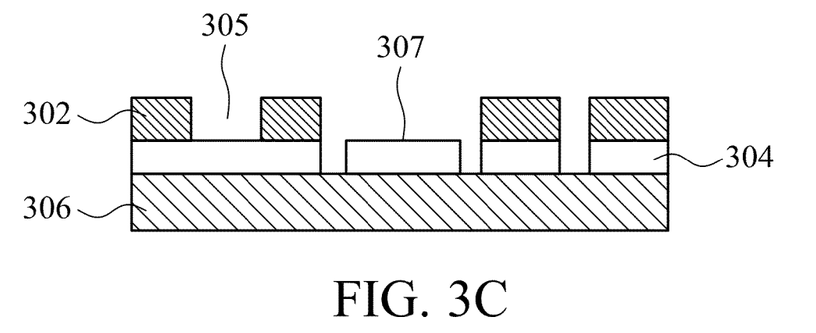

FIG. 3C illustrates a step of removing some portions 305 and 307 of the opaque layer 302, exposing some portions of the phase shift layer 304.

Figure 3D:
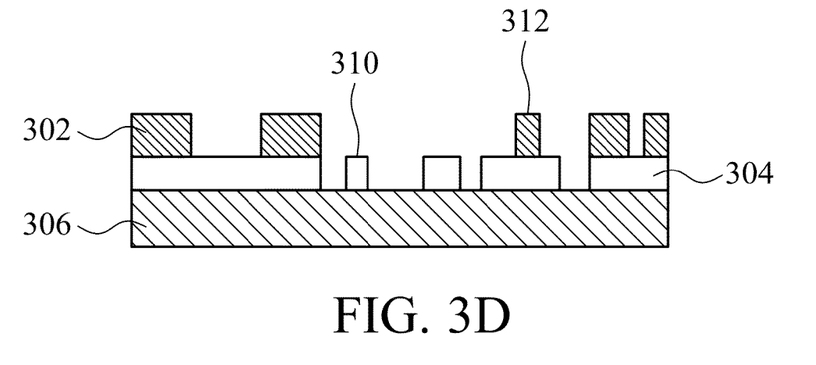

FIG. 3D shows a step of making simulated defects in the opaque layer 302 and the phase shift layer 304. As shown in FIG. 3D, the simulated defects may include silicon oxide particles or PSL particles 310 on an exposed portion of the substrate 306, and silicon oxide particles or PSL particles 312 on an exposed portion of the phase shift layer 304.

Thus, one embodiment of the present disclosure provides for the formation of a photomask (mask, or reticle, collectively referred to as mask) having a mask substrate and a mask pattern formed on the mask substrate. The mask may be utilized in manufacturing a semiconductor wafer. The mask substrate may be a transparent substrate such as fused silica ($SiO_2$), fused quartz, glass, calcium fluoride ($CaF_2$), or other suitable materials relatively free of defects.

The mask pattern on the mask substrate may include one or more features (or absorbers) formed of chromium (Cr) and one or more openings. In other embodiments, the mask pattern may include features formed of a metal silicide such as MoSi or $TaSi_2$, metal nitride, iron oxide, inorganic material, other materials such as Mo, $Nb_2O_5$, Ti, Ta, CrN, $MoO_3$, MoN, $Cr_2O_3$, TiN, ZrN, $TiO_2$, TaN, $Ta_2O_5$, $SiO_2$, NbN, $Si_3N_4$, ZrN, $Al_2O_3N$, $Al_2O_3R$, or combinations thereof.

In another embodiment, the mask pattern may include phase shift features formed above, on and/or at least partially in the substrate by etching thereof. The mask pattern may also be a binary intensity mask (BIM or binary mask) including chrome areas and transparent quartz areas. In another embodiment, the mask pattern may be an alternating phase shift mask (AltPSM), employing alternating areas of chrome and 180 degree-shifted quartz. In another embodiment, the mask pattern may be an attenuating phase shift mask (AttPSM), employing an attenuating feature having a phase shift relative to the transparent substrate. Alternatively, the mask pattern may be a chromeless phase shift pattern. In another embodiment, the mask pattern may include a combination of binary features and various phase shift features. Additionally, the mask pattern may include various optical proximity correction (OPC) features designed for fixing an optical proximity affect. The method of forming the mask pattern on the mask substrate may include chemical vapor deposition (CVD), physical vapor deposition (PVD), atomic layer deposition (ALD), plating, and/or other suitable processes.

The features of the mask pattern may be designed to attenuate and/or provide a phase shift to a radiation beam (or radiation energy), and the openings of the mask pattern may be designed to allow the radiation beam to pass through and expose a semiconductor wafer during a lithography patterning process. The radiation beam may include ultraviolet and/or may be extended to include other radiation beams such as deep ultraviolet (DUV), extreme ultraviolet (EUV), or other suitable radiation energy. For example, the radiation beam may include a 193 nm radiation beam from an Argon Fluoride (ArF) excimer laser or a 248 nm beam from a Krypton Fluoride (KrF) excimer laser.

Referring now to FIG. 4, a schematic diagram illustrates an example of contamination mode calibration using a pattern defect substrate as described in FIGS. 3A-3D according to an embodiment of the present invention. According to one aspect, FIG. 4 illustrates a schematic view of a bright field reticle inspection system 400. An example system is described in detail, e.g., by William H. Broadbent et al, in "Results from a new reticle defect inspection platform" in 23rd Annual BACUS Symposium on Photomask Technology, Proceedings of the SPIE, Volume 5256, pp. 474-488 (2003). The system 400 may use a high resolution microscope and linear sensor architecture, as opposed to the multi-beam laser scanner architecture of the system 100 of FIG. 1. Such an architecture offers several advantages to the laser scanner which include the potential for higher speed and no beam crosstalk.

System 400 includes an illumination source 402. By way of example, the illumination source 402 may be a 257-nm wavelength continuous wave (CW) laser. An active beam steering subsystem 404 compensates for beam drift and may also reduce replacement time for the light source 402. A transmitted light illuminator 406 may have several different configurations that can be selected by a user at run-time. For example one configuration may implement standard contrast for binary and EPSM reticles. Another configuration may implement phase contrast for quartz etch reticles such as alternating, chromeless, and the like. The phase contrast mode may provide improved imaging contrast to quartz phase defects (bumps and divots) allowing higher defect sensitivity.

A substrate 408 that is to be inspected is placed between the transmitted illuminator 406 and an imaging objective 410. In embodiments of the invention, the inspection system 400 may be used for contamination mode calibration, therefore substrate 408 may be a pattern defect substrate (e.g., as shown in FIG. 3D). In this example, the surface of the substrate 408 that includes a reticle pattern 409 faces the imaging objective 410. The substrate 408 may be scanned, e.g., using an air bearing stage. The reticle may be scanned along a first axis X for continuous image pick-up, and then indexed along a second axis Y after each swath to provide a serpentine inspection path.

The objective 410 images the reticle surface 409 through a zoom lens 412 onto an imaging sensor 414. The zoom lens 412 allows different pixel sizes to be selected by the user at run-time providing different defect sensitivities and associated scan times. Pixel sizes may be of any suitable size including, but not limited to, e.g., 72-nm, 90-nm, 125-nm and 150-nm pixel sizes. By way of example, the imaging sensor 414 may be a time-domain-integration (TDI) sensor. Such a sensor design offers high speed continuous image pick-up at much lower light levels than a conventional charge coupled device (CCD) linear sensor.

The system 400 also includes a reflected illumination optical path 416 which may be used during defect review to aid in the correct classification of contamination. Radiation may be coupled from the source 402 to the surface 409 of the substrate 408 via the reflected illumination optical path 416, a reflected illuminator 418 and a beamsplitter 420. The image sensor 414 may thus produce high resolution images 425 and 427 respectively showing transmitted and reflected images of portions of the substrate 408.

A pattern defect substrate may be used for contamination mode calibration according to an embodiment of the present invention. A standard substrate having simulated contamination defects with known characteristics is placed on an indexing and scanning stage of an inspection tool. By way of example, the inspection tool may be a bright field system, e.g., as shown in FIG. 1 or a bright field system, e.g., as in FIG. 4. In some embodiments, a dark field system may be used as the inspection tool. In one example, the pattern defect substrate is exposed to radiation having a wavelength of about 260 nanometers or less. The simulated defects on the standard substrate are stable over time under exposure to the radiation.

The inspection tool detects a pattern of light reflected by the substrate and a pattern of light transmitted through the substrate. A pattern of light transmitted through the standard substrate is predicted from the detected pattern of light reflected by the substrate, and a pattern of light reflected by the standard substrate is predicted from the detected pattern of light transmitted through the standard substrate. The contaminant defects may be determined by comparing the detected and predicted patterns of light reflected by the standard substrate or by comparing the detected and predicted patterns of light transmitted through the standard substrate. The inspection tool is then calibrated against the determined contaminant defects. The performance of the tool may be determined, e.g., by ascertaining whether the tool is able to locate simulated defects at known locations, or is able to accurately characterize properties of the simulated defects, e.g., their size distribution, when these properties are known.

As will be explained in greater detail below with respect to FIGS. 5 and 6A-6B, the substrate 408 as a test substrate or a calibration standard (e.g., a standard mask) includes a fluid layer over the substrate and the contamination defects or simulated contamination defects in one embodiment, thereby decreasing incident radiation wavelengths and increasing reflected or scattered radiation signals to enhance defect inspection analysis. In one example, the fluid has a refractive index greater than the refractive index of air.

Figure 5:
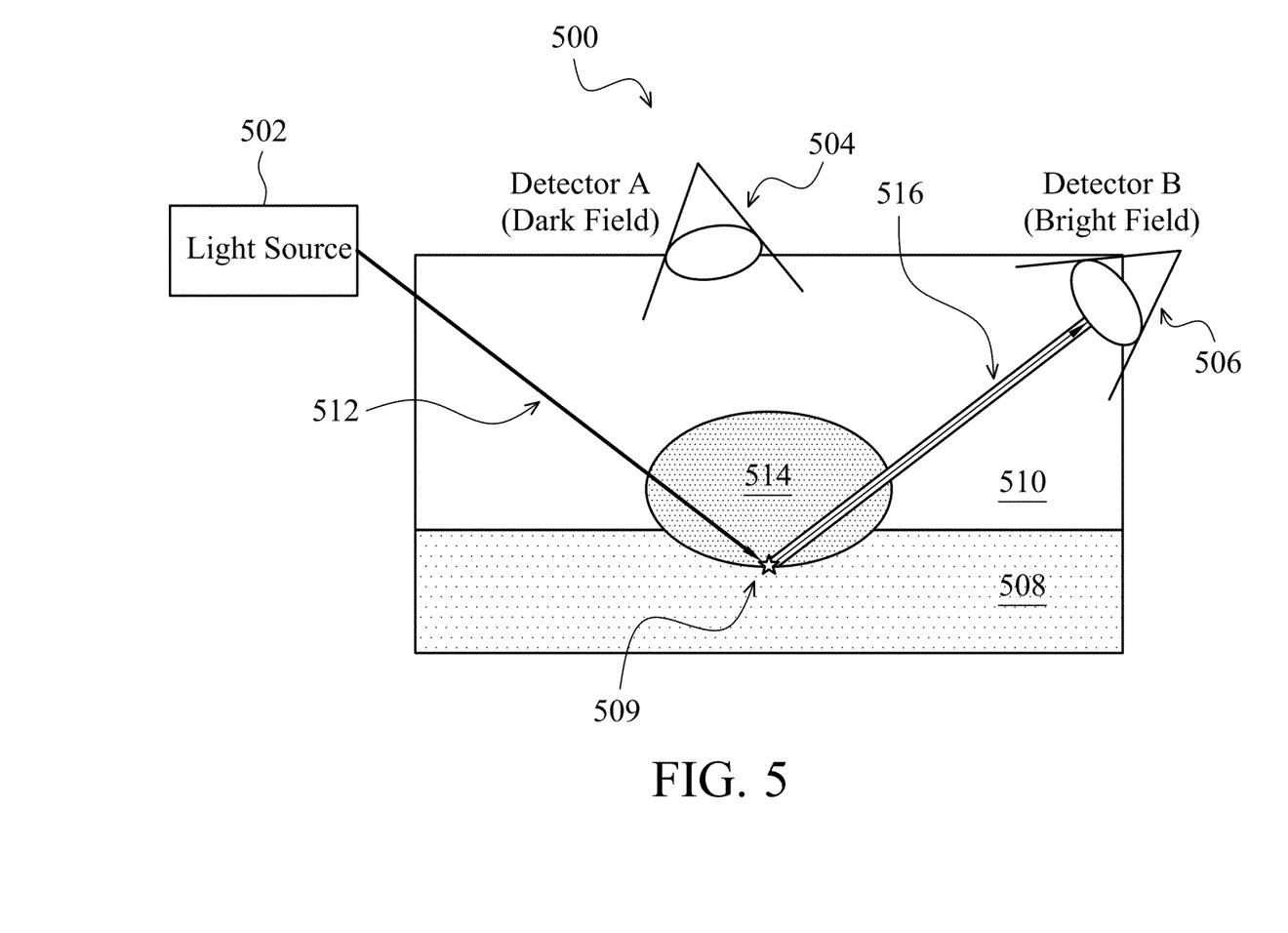
FIG. 5 is a cross-sectional schematic diagram illustrating a substrate having a defect and a fluid disposed over the substrate and the defect for enhanced defect inspection according to embodiments of the present disclosure.

Referring now to FIG. 5, a cross-sectional schematic diagram is shown illustrating a system 500 for enhanced defect inspection in accordance with embodiments of the present disclosure. According to one aspect, system 500 includes a light source 502, a platform or stage for holding a substrate 508, a first detector 504 (e.g., detector A for dark field inspection), and a second detector 506 (e.g., detector B for bright field inspection). The substrate 508 includes a defect particle 509 and a fluid 510 disposed over the substrate 508 and defect particle 509 in accordance with embodiments of the present disclosure. It is noted that the defect particle 509 may be on a test substrate or formed as part of a standard mask. The light source 502 exposes the substrate 508 and defect particle 509 to incident radiation 512 through the fluid 510. First detector 504 detects radiation 514 scattered by defect particle 509, and second detector 506 detects radiation 516 reflected by defect particle 509. Scattered radiation 514 and reflected radiation 516 are detected by first and second detectors 504 and 506, respectively, through the fluid 510.

Advantageously, the fluid 510 disposed over the substrate 508 and defect particle 509 causes incident radiation 512 to have a shorter wavelength and for scattered radiation 514 and reflected radiation 516 to have decreased angles of refraction as compared to traveling through air, to thereby enhance or strengthen signals for detection (as compared to not having a fluid 510 disposed over the substrate 508 and defect particle 509; i.e., radiation propagating through air).

According to one aspect of the present disclosure, fluid 510 may include water and/or another liquid. In another example, fluid 510 has a refractive index greater than air. Light source 502 may provide visible light, ultraviolet (UV) light, and/or deep ultraviolet (DUV) light. Although illustrated as two separate detectors in this embodiment, it should be noted that detectors 504 and 506 may be combined as a single unit detector in other embodiments.

Common elements in system 500 as those described above with respect to systems 100 and 400 (e.g., a light source, a detector, a substrate, and defect particle) may be substantially the same or similar and are fully applicable in this embodiment although repetitive description may not be included to avoid prolix description.

Figure 6A:
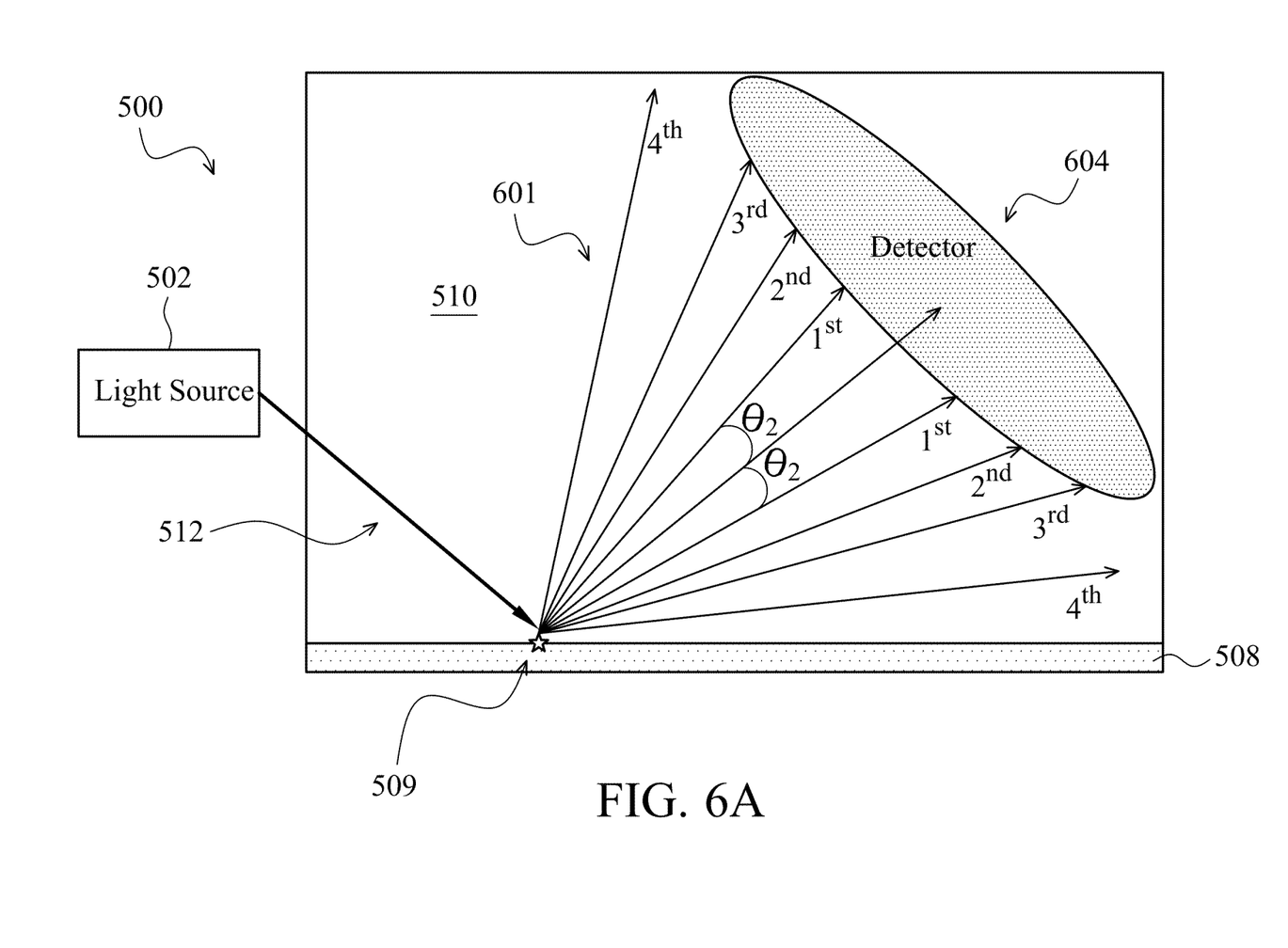
FIGS. 6A and 6B are cross-sectional schematic diagrams illustrating angles of refraction of scattered or reflected radiation through a liquid fluid and air medium, respectively, in accordance with embodiments of the present disclosure.
Figure 6B:
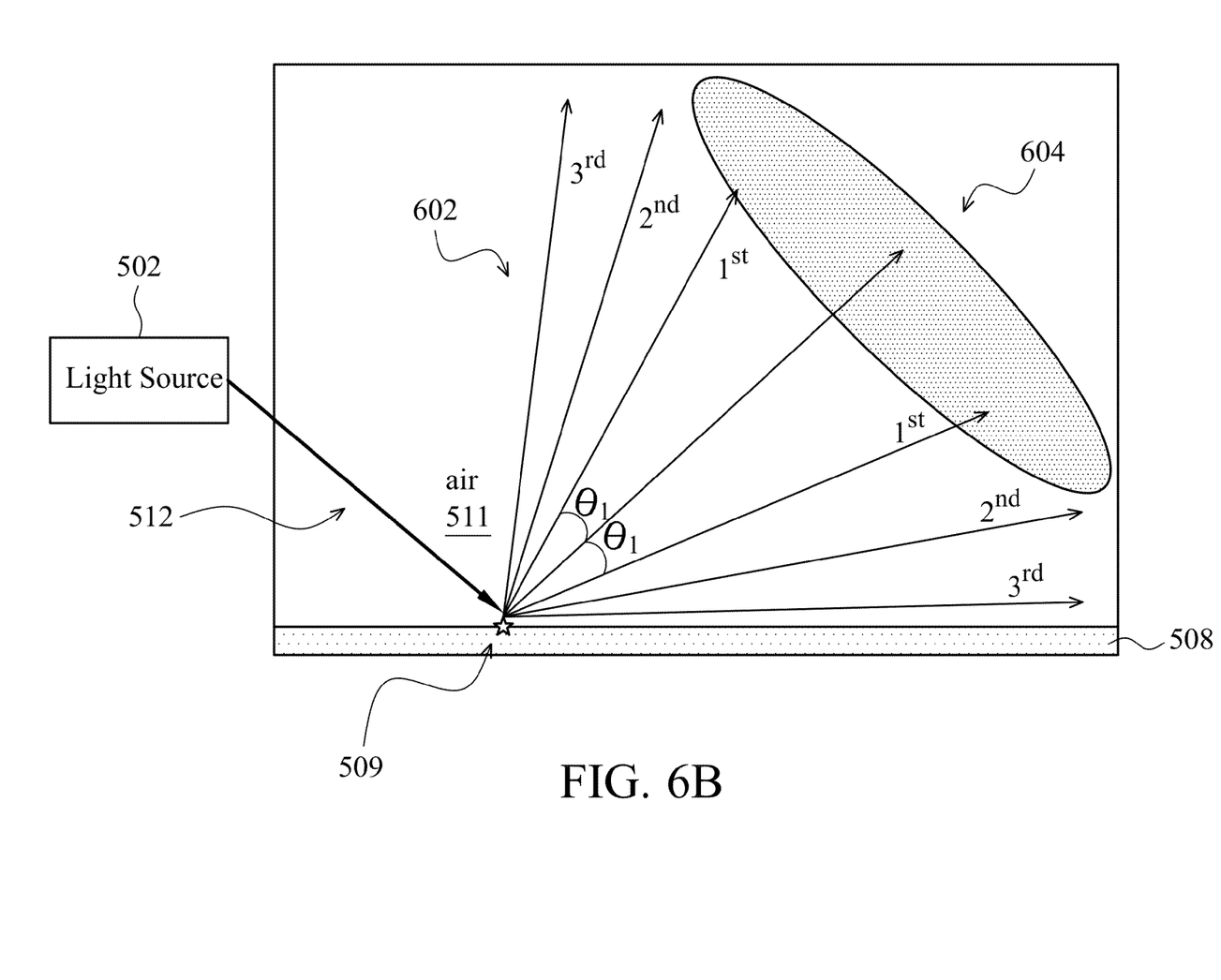

Referring now to FIGS. 6A and 6B, cross-sectional schematic diagrams illustrate angles of refraction theta ($\theta$) of scattered or reflected radiation through a liquid fluid 510 and air 511, respectively, disposed over the substrate 508 and defects 509, in accordance with embodiments of the present disclosure. Light source 502 exposes defect particle 509 to incident radiation 512 through fluid 510 and air 511, respectively, resulting in scattered or reflected radiation 601 and 602, respectively, to be detected by a detector 604. FIG. 6A illustrates angles of refraction $\theta_2$ of scattered or reflected radiation 601 through a liquid fluid 510 disposed over substrate 508 and defects 509, wherein the liquid fluid 510 has a higher refractive index $n_2$ than air, causing light to have wavelength $\lambda_2$ through the fluid medium 510. In comparison, FIG. 6B illustrates angles of refraction $\theta_1$ of scattered or reflected radiation 602 through air 511 having a refractive index $n_1$ and causing light to have wavelength $\lambda_1$ through the air medium.

In accordance with Snell's law, the angles of refraction, refractive indices, and wavelengths for the two mediums of fluid 510 and air 511 follow equations (2) and (3) below:

$$n_1 \sin(\theta_1) = n_2 \sin(\theta_2) \text{ or } n_1 \lambda_1 = n_2 \lambda_2 \quad (2)$$

$$\sin(\theta_2) = (n_1/n_2)\sin(\theta_1) \quad (3)$$

wherein
$n_1$ is the refractive index of air,
$n_2$ is the refractive index of fluid 510,
$\theta_1$ is the angle of refraction through air,
$\theta_2$ is the angle of refraction through fluid 510,
$\lambda_1$ is the wavelength of light through air, and
$\lambda_2$ is the wavelength of light through fluid 510.

Thus, if $(n_1/n_2) < 1$ or $n_2 > n_1$, then $\theta_2 < \theta_1$ and $\lambda_2 < \lambda_1$. In other words, when the refractive index of fluid 510 ($n_2$) is greater than the refractive index of air ($n_1$), the angle of refraction of light through the fluid ($\theta_2$) is shown to be advantageously decreased as compared to air to thereby enhance or strengthen the reflected or scattered light signals detected by detector 604 (e.g., detector 604 may capture $1^{st}$, $2^{nd}$, and $3^{rd}$ signals through fluid 510 (FIG. 6A) as compared to capturing only a $1^{st}$ signal through air (FIG. 6B)). Furthermore, when the refractive index of fluid 510 ($n_2$) is greater than the refractive index of air ($n_1$), the wavelength of light through the fluid ($\lambda_2$) is shown to be advantageously shorter as compared to the wavelength of light through air ($\lambda_1$), thereby improving scanning capability of an inspection system for detecting shrinking defect dimensions.

Figure 7:
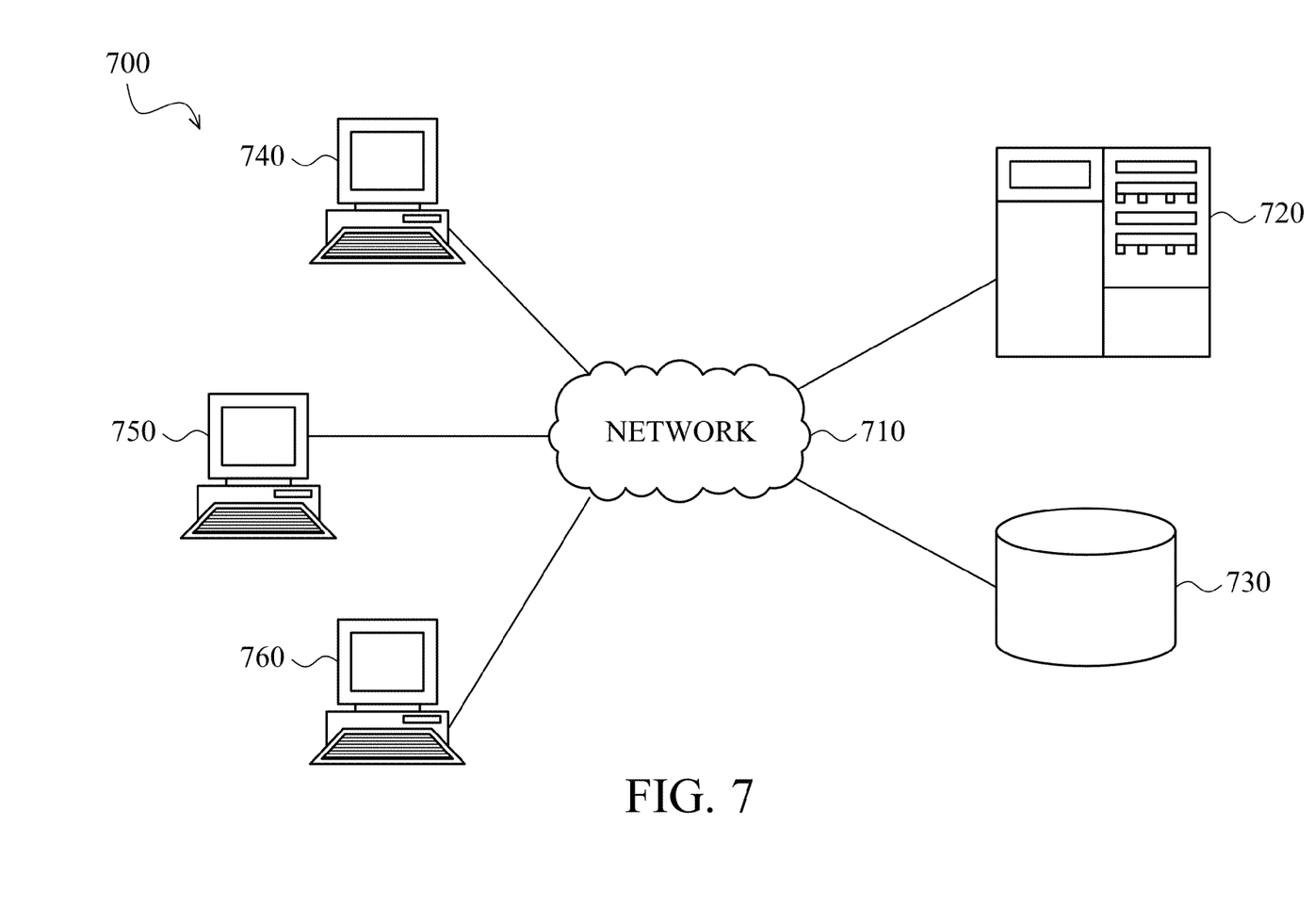
FIG. 7 illustrates a computing environment for performing the methods of the present disclosure in accordance with embodiments of the present disclosure.

Referring now to FIG. 7, a computing environment 700 is illustrated that may be used to implement the methods of the present disclosure described above. The computing environment 700 may be comprised of a network 710, which provides a medium through which various devices and computers in the computing environment can communicate. The network 710 may include connections such as wires, wireless, and/or fiber optic cables. The network 710 may further include the Internet and/or a collection of networks and gateways that use such things as a Transmission Control Protocol/Internet Protocol (TCP/IP) or other suitable protocols to communicate with. In another example, the network 710 may include a number of different types of networks such as a local area network (LAN), or a wide area network (WAN).

The computing environment 700 may be comprised of a server 720, a storage unit 730, and a plurality of clients 740, 750, 760. The plurality of clients 740, 750, 760 may include workstations, personal computers, or other suitable devices. The server 720 may provide applications and/or data stored in the storage unit 730 to the clients 740, 750, 760. Furthermore, the computing environment 700 may be comprised of additional nodes, such as additional servers, clients, and other devices not shown herein. FIG. 7 is intended to be a mere example, and is not an architectural limitation for the present disclosure.

Figure 8:
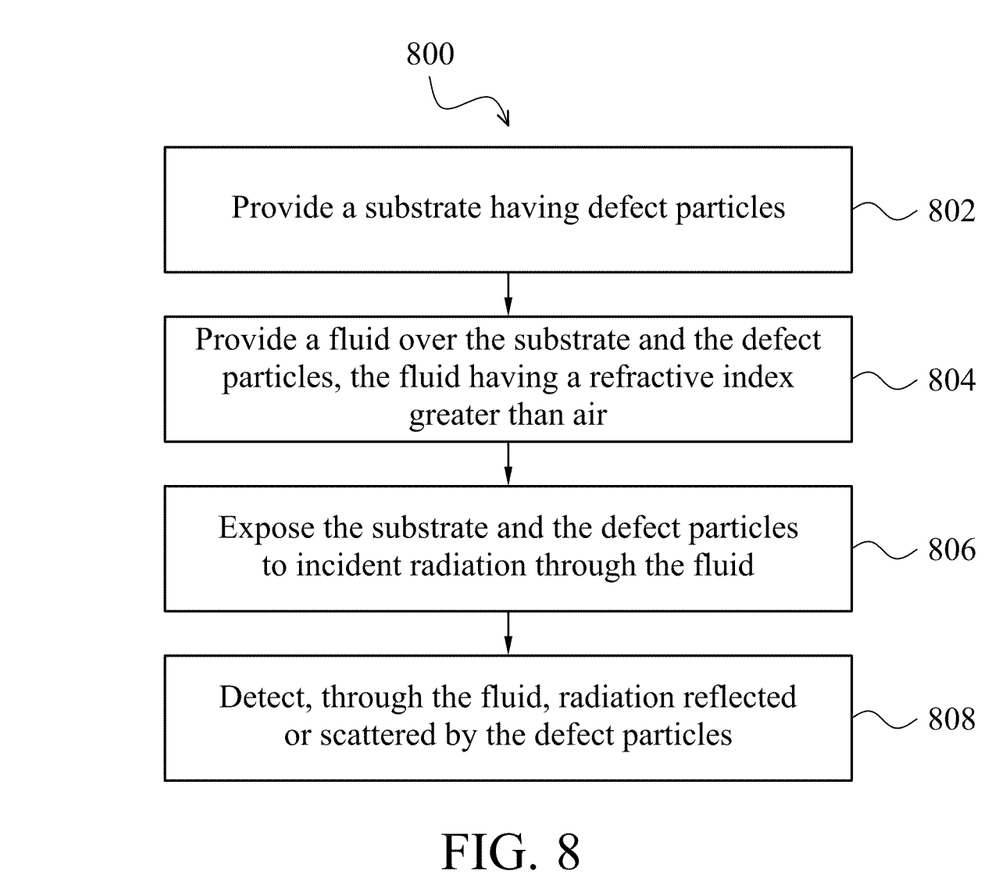
FIG. 8 is a flow diagram illustrating an example method of enhanced defect inspection according to an embodiment of the present disclosure.

In a more specific example, the method 800 of FIG. 8 and systems 100, 200, 400, and/or 500 of FIGS. 1, 2, 4, 5, and 6A, respectively, may be implemented within the computing environment 700. The clients 740, 750, 760 may be associated with the substrate inspectors and comparators between signals from mask standards and test substrates. The server 720 may provide the required data and/or software applications to the clients 740, 750, 760 to implement the method 800 of FIG. 8 to perform enhanced defect detection. The server 720 may also retrieve and store defect data generated by a comparator as well as image data generated by the substrate inspectors. Additionally, other clients such as a mask shop may communicate via the network 710 to receive defect data so that the mask shop can efficiently inspect and clean a photomask.

Referring now to FIG. 8, a flow diagram illustrates a method 800 for enhancing defect inspection. Method 800 includes providing a substrate having defect particles at block 802, and providing a fluid over the substrate and the defect particles at block 804, wherein the fluid has a refractive index greater than air. Method 800 further includes exposing the substrate and the defect particles to incident radiation through the fluid at block 806, and then detecting, through the fluid, radiation reflected or scattered by the defect particles at block 808.

It is noted that additional processes may be provided before, during, and after the method 800 of FIG. 8, and that some other processes may only be briefly described herein.

According to one aspect, providing the substrate includes providing a mask or a wafer, and providing the fluid includes providing water or another liquid. Advantageously, providing the fluid shortens the wavelength of incident radiation and decreases the angle of refraction of reflected or scattered radiation.

According to another aspect, method 800 may further include determining the defect particles with an inspection system by comparing a detected pattern of radiation reflected or scattered by the defect particles to a predicted pattern.

According to yet another aspect, method 800 may further include exposing the defect particles on the substrate to radiation of a known wavelength, measuring an amplitude of scattering of the radiation by the defect particles with an inspection system, comparing the amplitude of scattering of the radiation by the defect particles to an amplitude of scattering of radiation by standard defect particles of a standard mask, and then associating measured scattering of the radiation by the defect particles with a nominal size of standard defect particles.

In accordance with another embodiment, a method of inspecting a standard mask is provided. The method includes providing a substrate having standard defect particles and then providing a fluid over the substrate and the standard defect particles, wherein the fluid has a refractive index greater than air. The method further includes exposing the substrate and the standard defect particles to incident radiation through the fluid, and then detecting, through the fluid, radiation reflected or scattered by the standard defect particles.

Additional processes may be provided before, during, and after the method of inspecting a standard mask as described above. For example, providing the substrate includes providing a mask or a wafer. In another example, the standard defect particles may be comprised of silicon oxide or polystyrene latex, and the standard defect particles may be disposed as simulated contamination defects with known characteristics. In yet another example, providing the fluid includes providing water or another liquid. In yet another example, providing the fluid shortens the wavelength of incident radiation and decreases the angle of refraction of reflected or scattered radiation.

According to another aspect, the method for inspecting a standard mask may further include determining the standard defect particles with an inspection system by comparing a detected pattern of radiation reflected or scattered by the standard defect particles to a predicted pattern, and then calibrating the inspection system against the determined standard defect particles.

According to yet another aspect, the method for inspecting a standard mask may further include exposing the standard defect particles on the substrate to radiation of a known wavelength, measuring an amplitude of scattering of the radiation by the standard defect particles with the inspection system, and associating measured scattering of the radiation with a nominal size of the standard defect particles.

According to yet another aspect, the method for inspecting a standard mask may further include using an inspection system to measure an amplitude of scattering of the radiation by one or more localized scattering defects on a test substrate, and comparing the amplitude of scattering of the radiation by the one or more localized scattering defects on the test substrate to an amplitude of scattering of the radiation of standard defect particles of the standard mask.

The present disclosure provides for various advantageous methods and apparatus involved with contamination inspection of substrates. One of the broader forms of the present disclosure involves a method of enhanced defect inspection. The method includes providing a substrate having defect particles and providing a fluid over the substrate and the defect particles, the fluid having a refractive index greater than air. The method further includes exposing the substrate and the defect particles to incident radiation through the fluid, and detecting, through the fluid, radiation reflected or scattered by the defect particles.

Another of the broader forms of the present disclosure involves a method of inspecting a standard mask, the method comprising providing a substrate having standard defect particles; providing a fluid over the substrate and the standard defect particles, the fluid having a refractive index greater than air; exposing the substrate and the standard defect particles to incident radiation through the fluid; and detecting, through the fluid, radiation reflected or scattered by the standard defect particles.

Yet another of the broader forms of the present disclosure involves a system for defect inspection. The system includes a stage holding a substrate having defect particles and a fluid disposed over the substrate and the defect particles, a light source exposing the substrate and the defect particles to incident radiation through the fluid, and a detector detecting, through the fluid, radiation reflected or scattered by the defect particles.

Advantageously, the present disclosure provides for simultaneous shorter wavelengths of incident radiation and enhanced or strengthened scattered/reflected radiation for improved defect detection.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method of enhanced defect inspection, the method comprising:
   providing a substrate having defect particles;
   providing a fluid over the substrate and the defect particles, the fluid having a refractive index greater than air;
   exposing the substrate and the defect particles to incident radiation through the fluid;
   detecting, through the fluid, radiation reflected or scattered by the defect particles; and
   determining the defect particles with an inspection system by comparing a detected pattern of radiation reflected or scattered by the defect particles to a predicted pattern.

2. The method of claim 1, wherein providing the substrate includes providing a mask or a wafer.

3. The method of claim 1, wherein providing the fluid includes providing water or another liquid.

4. The method of claim 1, wherein providing the fluid shortens the wavelength of incident radiation.

5. The method of claim 1, wherein providing the fluid decreases the angle of refraction of reflected or scattered radiation.

6. The method of claim 1, further comprising:
   exposing the defect particles on the substrate to radiation of a known wavelength;
   measuring an amplitude of scattering of the radiation by the defect particles with an inspection system;
   comparing the amplitude of scattering of the radiation by the defect particles to an amplitude of scattering of radiation by standard defect particles of a standard mask; and
   associating measured scattering of the radiation by the defect particles with a nominal size of standard defect particles.

7. A method of inspecting a standard mask, the method comprising:
   providing a substrate having standard defect particles, wherein the standard defect particles are comprised of silicon oxide or polystyrene latex, and further wherein the standard defect particles are disposed as simulated contamination defects with known characteristics;
   providing a fluid over the substrate and the standard defect particles, the fluid having a refractive index greater than air;
   exposing the substrate and the standard defect particles to incident radiation through the fluid; and
   detecting, through the fluid, radiation reflected or scattered by the standard defect particles.

8. The method of claim 7, wherein providing the substrate includes providing a mask or a wafer.

9. The method of claim 7, wherein providing the fluid includes providing water or another liquid.

10. The method of claim 7, wherein providing the fluid shortens the wavelength of incident radiation and decreases the angle of refraction of reflected or scattered radiation.

11. The method of claim 7, further comprising:
    determining the standard defect particles with an inspection system by comparing a detected pattern of radiation reflected or scattered by the standard defect particles to a predicted pattern; and
    calibrating the inspection system against the determined standard defect particles.

12. The method of claim 7, further comprising:
    exposing the standard defect particles on the substrate to radiation of a known wavelength;
    measuring an amplitude of scattering of the radiation by the standard defect particles with the inspection system; and
    associating measured scattering of the radiation with a nominal size of the standard defect particles.

13. The method of claim 7, further comprising:
    using an inspection system to measure an amplitude of scattering of the radiation by one or more localized scattering defects on a test substrate; and
    comparing the amplitude of scattering of the radiation by the one or more localized scattering defects on the test substrate to an amplitude of scattering of the radiation of standard defect particles of the standard mask.

14. A system for defect inspection, comprising:
    a stage holding a substrate having defect particles and a fluid disposed over the substrate and the defect particles;
    a light source exposing the substrate and the defect particles to incident radiation through the fluid;
    a detector detecting, through the fluid, radiation reflected or scattered by the defect particles; and
    a comparator measuring an amplitude of scattering of the radiation by one or more localized scattering defects on a test substrate and comparing the amplitude of scattering of the radiation by the one or more localized scattering defects on the test substrate to an amplitude of scattering of the radiation of standard defect particles of a standard mask.

15. The system of claim 14, wherein the fluid includes water and/or another liquid.

16. The system of claim 14, wherein the fluid shortens the wavelength of incident radiation and decreases the angle of refraction of reflected or scattered radiation.

17. The system of claim 14, wherein the light source provides visible light, ultraviolet light, and/or deep ultraviolet (DUV) light.

18. The system of claim 14, wherein the detector provides a dark field inspection or a bright field inspection.

* * * * *